(12) United States Patent
Cantrell

(10) Patent No.: US 6,991,604 B2
(45) Date of Patent: Jan. 31, 2006

(54) DUAL BLADE LARYNGOSCOPE WITH ESOPHAGEAL OBTURATOR

(75) Inventor: Elroy T. Cantrell, Huntsville, TX (US)

(73) Assignee: Scope Co, Inc., Roanoke, VA (US)

( * ) Notice: Subject to any disclaimer, the term of this patent is extended or adjusted under 35 U.S.C. 154(b) by 0 days.

(21) Appl. No.: 10/931,537

(22) Filed: Sep. 1, 2004

(65) Prior Publication Data

US 2005/0054903 A1   Mar. 10, 2005

Related U.S. Application Data

(60) Provisional application No. 60/500,107, filed on Sep. 4, 2003.

(51) Int. Cl.
*A61B 1/267* (2006.01)

(52) U.S. Cl. .................. 600/194; 600/185; 600/190; 600/197; 600/199

(58) Field of Classification Search .............. 600/185, 600/190, 194–197
See application file for complete search history.

(56) References Cited

U.S. PATENT DOCUMENTS

| | | | |
|---|---|---|---|
| 1,568,732 A | * | 1/1926 | Haslinger .............. 600/196 |
| 2,854,004 A | | 9/1958 | Durrant |
| 4,126,127 A | | 11/1978 | May |
| 4,314,551 A | | 2/1982 | Kadell |
| 4,384,570 A | | 5/1983 | Roberts |
| 4,517,964 A | | 5/1985 | Upsher |
| 4,825,858 A | * | 5/1989 | Frankel ............ 128/200.26 |
| 5,016,614 A | * | 5/1991 | MacAllister .......... 600/131 |
| 5,287,848 A | | 2/1994 | Cubb et al. |
| 5,339,805 A | * | 8/1994 | Parker ............ 128/200.26 |
| 5,498,231 A | | 3/1996 | Franicevic |
| 5,595,172 A | | 1/1997 | Reese |
| 5,702,351 A | | 12/1997 | Bar-Or et al. |

(Continued)

OTHER PUBLICATIONS

Walls, "Section 1 Resuscitation: Chapter 1 Airway Management," Rosens Emergency Medicine Concepts and Clinical Practice, 4th ed., p. 2-24.

*Primary Examiner*—Beverly M. Flanagan
*Assistant Examiner*—Matthew J. Kasztejna

(57) ABSTRACT

A dual bladed laryngoscope for quickly and easily intubating a patient. The invention has two blades pivotally hinged on one side while the opposing side is open allowing the laryngoscope to be easily removed after intubating a patient. The proximal end of the upper blade has a grip portion which can be moved closer to or farther away from the handle attached to the proximal end of the lower blade to open or close the distal ends of the lower and upper blades. The lower blade of the invention has a distal end adapted as an esophageal obturator for obstructing the esophagus. An arytenoid bumper to prevent the laryngoscope from penetrating too far into the esophagus is preferably secured to the distal end of the lower blade. The arytenoid bumper may have a ramp or wedge shape adapted to deflect an intubation tube through a patient's larynx and into the trachea. The upper blade optionally has a tongue guard adapted to hold the tongue outside of a channel formed by the lower blade, the tongue guard and the upper blade. A suction conduit is optionally built in or secured to either the lower blade or the upper blade for providing a tube for suctioning secretions or emesis. A suction break is located in the handle of the laryngoscope to allow a finger of the hand holding the laryngoscope to control the presence and intensity of suction.

32 Claims, 5 Drawing Sheets

U.S. PATENT DOCUMENTS

| | | |
|---|---|---|
| 5,897,489 A * | 4/1999 | Urbanowicz et al. ....... 600/185 |
| 5,938,591 A | 8/1999 | Minson |
| 5,993,383 A | 11/1999 | Haase |
| 6,095,972 A | 8/2000 | Sakamoto |
| 6,142,144 A | 11/2000 | Pacey |
| 6,174,281 B1 | 1/2001 | Abramowitz |
| 6,217,514 B1 | 4/2001 | Gruen |
| 6,231,505 B1 | 5/2001 | Martin |
| 6,248,061 B1 | 6/2001 | Cook, Jr. |
| 6,354,993 B1 | 3/2002 | Kaplan |
| RE37,861 E | 9/2002 | Schneider |
| 6,471,643 B1 | 10/2002 | Henderson |
| 6,672,305 B2 * | 1/2004 | Parker ................... 128/200.26 |
| 6,749,563 B2 * | 6/2004 | Stihl .......................... 600/196 |

* cited by examiner

DUAL BLADE LARYNGOSCOPE WITH ESOPHAGEAL OBTURATOR

CROSS REFERENCE TO RELATED APPLICATION

Priority is claimed to U.S. Provisional Patent Application Ser. No. 60/500,107 filed by the inventor on Sep. 4, 2003, which is incorporated by reference.

BACKGROUND OF THE INVENTION

1. Field of the Invention

The present invention relates to a medical device for intubating a patient, and more particularly to a dual-bladed laryngoscope.

2. Description of the Related Art

It is often necessary to put a tube in a person's airway for assisting in breathing, such as emergency situations where a patient or victim is no longer able to breath normally, or during anesthesia or cardiac arrest to prevent aspiration of mucus, vomit, or particulate matter into the lungs. This procedure is referred to as endotracheal intubation. A laryngoscope may be used to assist a caregiver in performing this procedure. Laryngoscopes may be comprised of a single blade, which may be straight or curved for guiding the tube into the trachea, or comprised of two blades. A dual-bladed laryngoscope has two opposing blades that are connected by a pair of hinge points, and each blade has a handle in proximate relationship to each other for opening distal ends of the blades which then open a passageway through a patient's mouth and larynx into which an endotracheal tube may be passed. Laryngoscopes are often fitted with a light for illuminating the passageway for easier insertion of the laryngoscope and the intubation tube.

The intubation process is often difficult due to anatomic or pathologic differences between individuals. The most common error in intubation is placing the tube in the esophagus instead of the trachea when the caregiver cannot adequately see the trachea or vocal cords. Failure to recognize this error can lead to fatal hypoxia in an intubated patient, and some studies have shown a failure rate of up to 30% for intubations made in the field.

In an effort to minimize this failure rate, some laryngoscopes include fiber optics for visualizing the vocal cords for proper tube placement, however these devices are very expensive and are not widely available. Other devices have been developed as alternatives to endotracheal intubation, such as the Esophogeal Obturator Airway (EOA), the Esophagogastric Tube Airway (EGTA), the Esophageal Tracheal Combitube, and the Laryngeal Mask Airway (LMA). These devices are designed to allow "blind" intubation without the operator actually visualizing the vocal cords and trachea. The EOA lacks proven effectiveness and is considered dangerous by design. The EGTA is a variant of the EOA and suffers from the same drawbacks. It was a predecessor to the Combitube. Regarding the Combitube and the LMA, experts maintain that these devices should only be used temporarily until definitive airway management can be achieved through endotracheal intubation. Therefore, there is still work to be done in simplifying the endotracheal intubation process and ensuring proper and definitive airway management.

U.S. Pat. No. 5,498,231, issued to Franicevic on Mar. 12, 1996, is incorporated by reference for all purposes, including alternatives and equivalents for various elements of the presently claimed invention. The Franicevic invention is directed to a laryngoscope comprising an elongate hollow body consisting of two hollow tubes with a pair of opposed blades pivotally mounted to the distal end of the hollow body. These blades are perpendicular to the hollow body and pivotal on their axes so that the blades may assume an open or closed position. A complicated rack and pinion gear system is used to open the blades. An endotracheal tube can be passed through the hollow body and between the blades via a tube introducor. A sophisticated steering mechanism allows the tube introducer to steer the endotracheal tube into the trachea. A fiberoptic optical system with illumination is provided for observation during the intubation procedure. The primary disadvantage of this art is that the fiber optics and complicated design make it very expensive. Another disadvantage is that you must disassemble the endotracheal tube by removing the proximal fitting that connects the tube to an oxygen source in order to remove the laryngoscope, and there is no mechanism for blocking the esophagus to ensure proper tube placement in the trachea. In addition, the design of this laryngoscope makes it impossible to suction the patient without removing the entire laryngoscope first. This wastes valuable seconds when trying to establish a patent airway for a patient.

U.S. Pat. No. 5,938,591, issued to Minson on Aug. 17, 1999 provides a good review of the prior art on laryngoscopes and is incorporated by reference for all purposes, including alternatives and equivalents for various elements of the presently claimed invention. Minson describes a disposable, curved, dual-bladed laryngoscope with light conductive blades that open and lock apart laterally and/or radially. The blades are separated and locked apart using a ratchet mechanism in the handle that allows the device to be self-retaining in the airway. However, other than illuminating the airway, this device provides no other assistive mechanisms to increase the ease and accuracy of intubation. In addition, in order to suction a patient, a suction device must be passed through the laryngoscope first and then removed before the endotracheal tube can be inserted into the airway. If the patient vomits before the endotracheal tube is properly inserted, the tube must be removed, a suction device inserted, used, and removed, and then the endotracheal tube reintroduced through the laryngoscope. This exchanging of tubes can waste valuable seconds when seconds really count. Minson also teaches that the laryngoscope may be left in the throat after the endotracheal tube is placed in the trachea. If this occurs, his laryngoscope will have to be removed during the time one oxygen source is exchanged for another. This could add precious seconds to the time a patient is without oxygen during this exchange.

The following U.S. Pat. Nos. claim areas of innovations in laryngoscopes: U.S. Pat. Nos. 4,314,551; 4,384,570; 4,517,964; 5,993,383; 6,095,972; 6,174,281; 6,217,514; 6,231,505; 6,354,993; 6,471,643 and RE 37,861. However, these devices do not include features to decrease the likelihood of missed intubation, they are difficult to remove after insertion of the endotracheal tube, and they lack the ability to easily suction the patient using the same hand as the one holding the laryngoscope. In fact, none of the related art contains these features, all of which could improve the likelihood of proper tube placement and simplify the intubation process for the caregiver.

While there are suction devices that are operated independently of a laryngoscope, there are none that are integral to the laryngoscope itself. While U.S. Pat. No. 5,595,172 issued to Reese on Jan. 21, 1997, teaches suction through an endotracheal tube operated by a finger, this device is separate from the laryngoscope and in fact functions as a stylet for the endotracheal tube. This device is operated using the right hand while the left hand holds the laryngoscope. Once the endotrachreal tube is in place, the suction mechanism must be removed from the tube while keeping the tube stabilized with the right hand and still holding the laryngoscope with the left hand. This process is awkward and unwieldy.

SUMMARY OF THE INVENTION

A laryngoscope is provided that has a lower blade and an upper blade pivotally connected to the lower blade, where the lower blade has a distal end adapted as an esophageal obturator for obstructing the esophagus. An arytenoid bumper is preferably secured to the lower blade near the distal end, and the arytenoid bumper may have a ramp or wedge shape and be adapted to direct an intubation tube through a patient's larynx into the trachea. A laryngoscope is also provided that has a lower blade and an upper blade pivotally connected to the lower blade, where the pivotal connection is on one side and the opposing side is open so that the laryngoscope may be removed after intubating a patient while leaving the intubation tube in place. The upper blade has a grip portion near the proximal end, and the grip portion can be moved closer to or farther away with respect to the proximal end of the lower blade to open or close the distal ends of the lower and upper blades with respect to one another. The upper blade optionally has a tongue guard adapted to hold the tongue outside of a channel formed by the lower blade, the tongue guard and the upper blade. Further, a laryngoscope is provided that has a suction tube is optionally built in or secured to either the lower blade or the upper blade for providing a conduit for suctioning. The suction tube is preferably adapted for receiving a vacuum source on a proximal end. The suction tube preferably has a distal end with one or more openings for suctioning while an intubation tube is inserted into a patient's air way.

DETAILED DESCRIPTION OF THE INVENTION

1. Preferred Embodiment.

The present invention is directed to a dual-bladed laryngoscope adapted for blocking the opening to the esophagus and preventing a tube from entering the esophagus during intubation. The laryngoscope preferably includes a ramp for guiding the intubation tube into the trachea. Another aspect of the invention includes a hinge connection between the two blades, where one side of the two blades are pivotally connected with the other side open so that an intubation tube may remain in place while the laryngoscope is removed. The intubation tube passes through the open side of the laryngoscope. The laryngoscope may further include a tongue guard for holding the tongue out of the way when forming a passageway through which to guide an intubation tube, a light for illuminating the passageway thus formed, and an integrated suction tube operated by a finger of the hand holding the laryngoscope.

Figure 1:
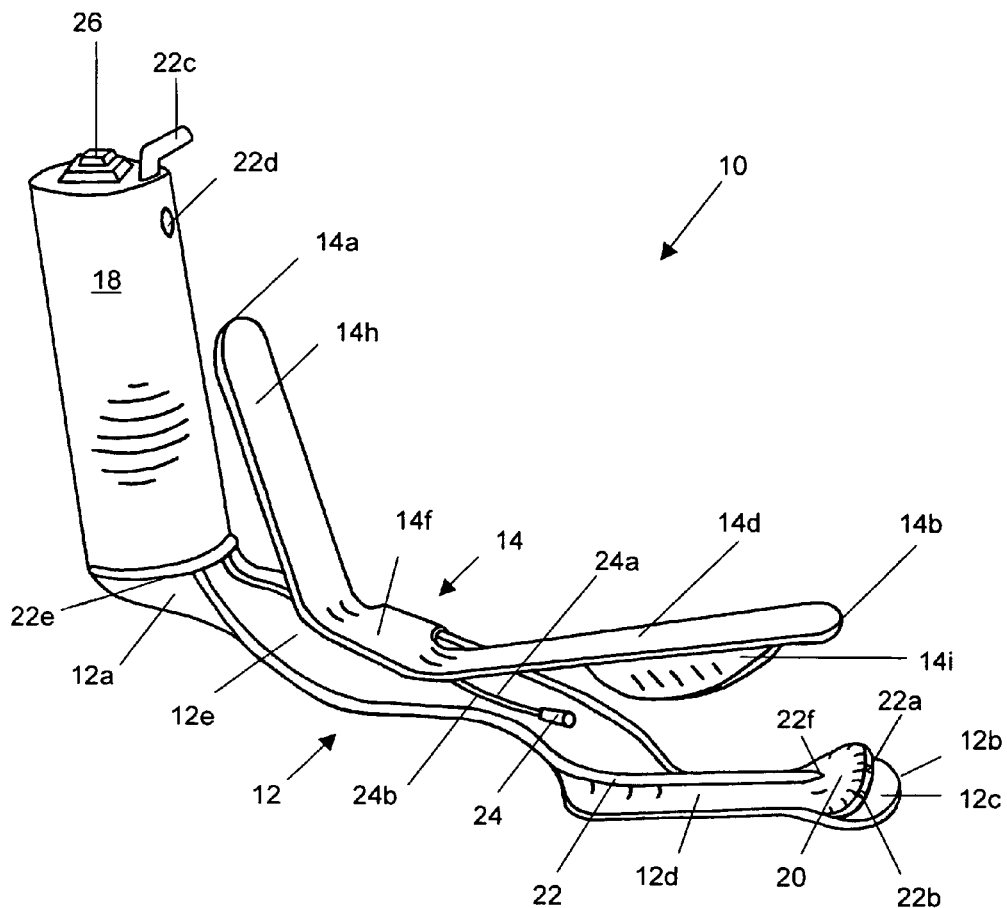
FIG. 1 is a perspective view of a laryngoscope, according to the present invention.

With reference to FIG. 1, one embodiment of a laryngoscope 10 is shown in perspective view according to the present invention. Laryngoscope 10 includes a lower blade 12 and an upper blade 14 connected by a pin 16 (shown in FIGS. 2 and 3), which provides a hinged or pivotal connection for lower and upper blades 12 and 14, respectively. Lower and upper blades 12 and 14 have proximal ends 12a and 14a, respectively, and lower blade 12 has a handle 18 on proximal end 12a.

Lower blade 12 has a distal end 12b. Distal end 12b is adapted to form an esophageal obturator 12c. Esophageal obturator 12c covers and partially enters the esophagus when inserted into a patient's mouth to prevent an intubation tube from passing into the esophagus. The esophageal obturator can be oval, round, spherical or otherwise suitably shaped for insertion into the esophagus, preferably to a distance of greater than ¼ of an inch and less than about 1 inch, more preferably between ½ inch and about ¾ of an inch.

An arytenoid bumper 20 is attached to the lower blade 12 near distal end 12b. Arytenoid bumper 20 is wider than flat or horizontal portion 12d of lower blade 12 and is preferably adapted for the size of the patient. Arytenoid bumper 20 stabilizes the position of laryngoscope 10 while inserted so as to position esophageal obturator 12c over and within the esophagus. Arytenoid bumper 20 is generally shaped like a wedge and provides a ramp to guide an intubation tube sliding along lower blade 12 distally toward the upper blade, through the vocal cords, and into the trachea. The ramp is oriented so that the thin edge of the ramp is toward the proximal end or hinge, and the thicker edge is toward distal end 12b. Arytenoid bumper 20 may be made as part of lower blade 12 or as an attachment to lower blade 12. Factors such as cost and ability to sterilize should be considered in determining how to make arytenoid bumper 20. Arytenoid bumper 20 is generally wider than lower blade 12, and lower blade 12 may be as wide as arytenoid bumper 20 in conformance with the width of arytenoid bumper 20 and narrower elsewhere, or arytenoid bumper 20 can extend over both sides of lower blade 12.

A suction conduit 22 enters the laryngoscope at the suction fitting 22c located on the top of handle 18. A suction break 22d opens to the air and allows a finger to control the presence and intensity of suction. The suction conduit 22 exits the handle 18 at exit point 22e and continues down the lower blade 12 and enters arytenoid bumper 20 at point 22f. The suction conduit then splits into two separate suction ports 22a and 22b located on the face of arytenoid bumper 20.

Lower blade 12 comprises a flat or horizontal portion 12d that includes distal end 12b on one end. A vertical portion 12e of lower blade 12 is attached to the lateral proximal end of flat or horizontal portion 12d of lower blade 12. Vertical portion 12e sweeps away from flat or horizontal portion 12d at about a 45 degree angle in a direction away from distal end 12b. The angle of vertical portion 12e to flat or horizontal portion 12d can be varied for comfort and operability between an angle of about 15 degrees and about 75 degrees, preferably between about 30 degrees and about 60 degrees in an arc and sweep rather than form a straight line.

Lower blade 12 has a hinge pin 16 (shown in FIGS. 2 and 3) centrally located in the vertical portion 12e. The pin 16 (shown in FIGS. 2 and 3) connects upper blade 14 to lower blade 12. Lower blade 12 has an L-shaped cross section formed by the flat or horizontal portion 12d and vertical portion 12e. The L-shaped cross section adds strength and rigidity to lower blade 12. The vertical portion 12e of lower blade 12 transitions into a fitting at its proximal end 12a that is attached to handle 18. The general shape of the vertical portion 12e of lower blade 12 may be sigmoid in order to avoid contact with a patient's teeth. Proximal end 12a is oriented at about 80 or 90 degrees with respect to handle 18, and a side view of lower blade 12 has somewhat of an L shape, but rather than a sharp corner, there is a gentle rise in transition from the flat or horizontal portion 12d to the vertical leg 12e of lower blade 12.

Handle 18 on proximal end 12a is adapted to fit a battery (not shown) as an energy source for a lamp 24 connected by a pair of wires 24a and 24b to a switch 26. Switch 26 may be a button that can be operated by a thumb and it may be a trigger switch or any other mechanism for providing a switch in a circuit comprising lamp 24 wires 24a and 24b and the battery inside handle 18.

Upper blade 14 has a distal end 14b opposing proximal end 14a. Upper blade 14 has a flat or horizontal portion 14d that is generally parallel with flat or horizontal portion 12d of lower blade 12, depending on the pivotal position of one blade with respect to the other. Distal end 14b of upper blade 14 does not extend as far as distal end 12b of lower blade 12, instead ending about midway of the arytenoid bumper 20. Upper blade 14 does not have a portion corresponding to vertical portion 12e of lower blade 12, and flat or horizontal portion 14d extends from distal end 14b to a hinge portion 14f. Flat or horizontal portion 14d of upper blade 14 is adapted with a length such that esophageal obturator 12c can be placed over the esophagus with arytenoid bumper 20 lodged in place while flat or horizontal portion 14d of upper blade 14 can be used to lift and separate soft tissue inside the patient's throat to provide a visible opening through which an intubation tube can be passed.

Hinge portion 14f transitions into a grip portion 14h that extends from hinge portion 14f to proximal end 14a. Grip portion 14h has a general shape of a flat bar and is roughly a 90 degree angle with respect to flat or horizontal portion 14d of upper blade 14, more preferably about a 100 degree angle or so and maybe as high as 110 or 120 degrees. Grip portion 14h is adjacent to handle 18 on lower blade 12 and is adapted so that a care giver can use the palm and thumb of one hand engaged with handle 18 while his or her fingers are engaged with grip portion 14h. By gently squeezing grip portion 14h towards handle 18, upper blade 14 pivots with respect to lower blade 12, increasing the distance between distal ends 12b and 14b and opening the two blades to provide an unobstructed passageway through which an intubation tube can be inserted through a patient's mouth and larynx into the trachea without inadvertent passage into the esophagus.

The hinge portion 14f has a tab forming an L-shaped cross section with the hinge portion 14f. The tab forms the hinge connecting the upper blade 14 to the vertical portion 12e of lower blade 12. Hinge portion 14f is relatively short with respect to flat or horizontal portion 14d of upper blade 14 or with respect to grip portion 14h. Hinged portion 14f is angled at about 30 to about 50 degrees with respect to flat or horizontal portion 14d and similarly with respect to grip portion 14h.

The vertical portion of the L shape of flat or horizontal portion 14d of upper blade 14 provides a tongue guard 14i, which has the shape of a normal bell shaped curve extending toward lower blade 12. Tongue guard 14i is adapted to hold a patient's tongue to one side while an intubation tube is inserted through the patient's larynx into the trachea. In the closed position, tongue guard 14i may partially overlap vertical portion 12e of lower blade 12 in a scissor-like arrangement.

Figure 2:
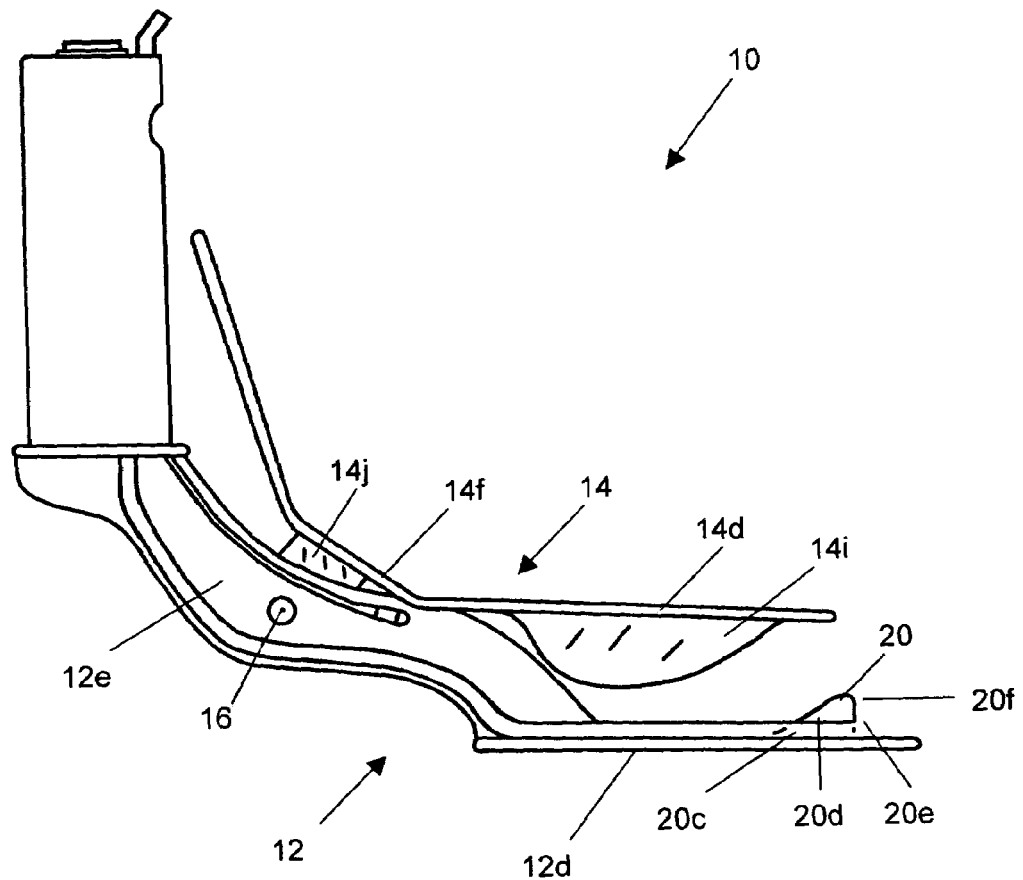
FIG. 2 is a side elevation of the laryngoscope of FIG. 1, according to the present invention.

Turning now to FIG. 2, a side view of laryngoscope 10 is shown according to the present invention. A like number between FIG. 2 and FIG. 1 indicates a like element. It can be seen in FIG. 2 that arytenoid bumper 20 has a thin proximal edge 20c leading into an inclined surface 20d that terminates in a peak 20e and a vertical side 20f that represents the thickness of arytenoid bumper 20 at its distal end. It can be seen in the side view, which shows pin 16 in cross-section, that hinge portion 14f of upper blade 14 has an L-shaped tab 14j forming the hinge connecting the upper blade 14 to the vertical portion 12e of lower blade 12 by pin 16.

Tongue guard 14i can be seen to have a shape generally of a normal bell-shaped curve, but with the curve skewed toward the proximal end. Tongue guard 14i located on the left edge of flat or horizontal portion 14d of upper blade 14 forms an L-shape in cross section and is approximately centered on flat or horizontal portion 14d of upper blade 14.

Figure 3:
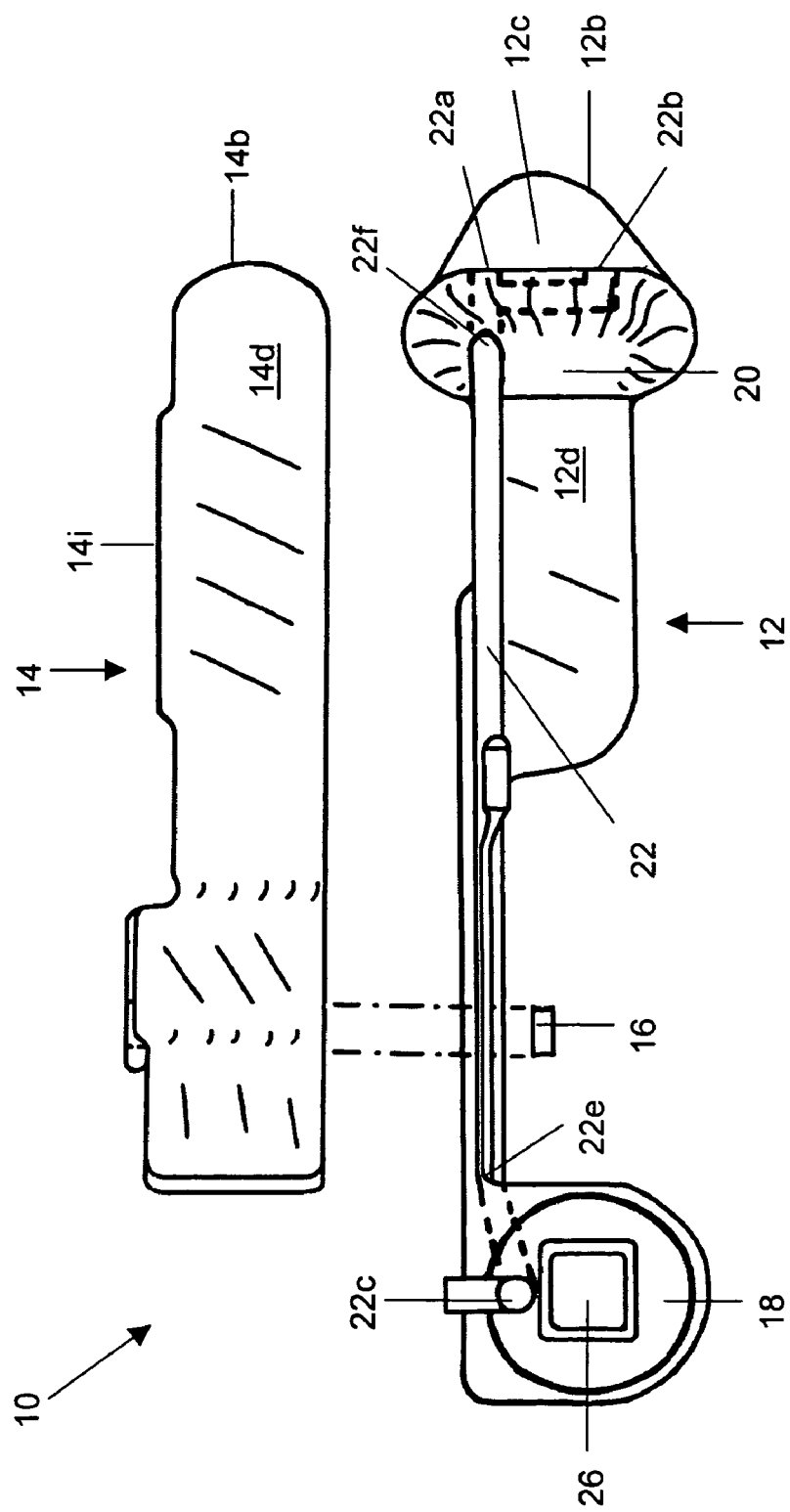
FIG. 3 is a top view of the laryngoscope of FIG. 2, but with the upper blade separated from the lower blade, and a dashed line shows the location of a hinge connection.

With reference to FIG. 3, laryngoscope 10 is shown in a top view, but also as an exploded view to see separately the top side of each of blades 12 and 14. Switch 26 is shown on the top of handle 18. Suction fitting 22c is also located on the top of handle 18. Suction conduit 22 exits the handle 18 at exit point 22e, traverses across lower blade 12 and enters arytenoid bumper 20 at point 22f. Suction ports 22a and 22b are indicated by dashed lines inside of arytenoid bumper 20. The relative position of pin 16 is shown by a pair of interrupted lines connecting upper blade 14 to lower blade 12.

A top view of arytenoid bumper 20 is shown as a bulbous shape that is generally wider than flat portion 12d of lower blade 12. Esophageal obturator 12c is shown as having a generally tapered and rounded shape as it transitions from essentially the width of flat or horizontal portion 12d of lower blade 12 to a point at distal end 12b. Esophageal obturator 12c may either insert inside the esophagus, hence an appropriate shape is needed, or may overlay and cover the esophagus, requiring a different shape.

In contrast, distal end 14b of upper blade 14 preferably has a much blunter tip, which is preferably flat. Tongue guard 14i is not particularly visible, but the top edge can be seen to protrude from an outside edge of flat or horizontal portion 14d of upper blade 14 a distance of the thickness of tongue guard 14i.

Figure 4:
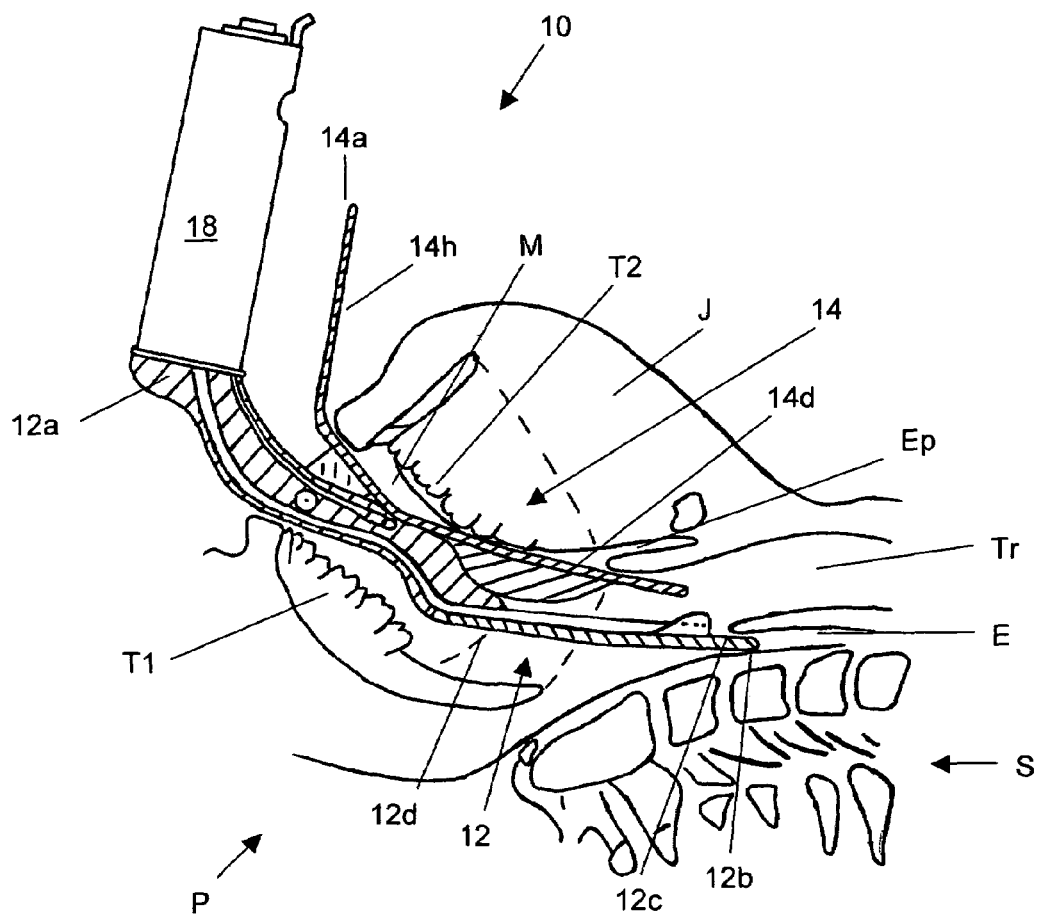
FIG. 4 is a side view of the laryngoscope of FIG. 1 inserted through a patient's mouth with the laryngoscope in the closed position, according to the present invention.

Turning to FIG. 4, a side view of laryngoscope 10 is shown in a closed position inserted into position through the mouth M of a patient P lying supine. The patient's jaw J, upper teeth T1, and lower teeth T2 are shown as well as the spine S. The patient's trachea is shown as Tr, esophagus as E and epiglottis as Ep.

Distal end 12b of lower blade 12 passes through the mouth M and esophageal obturator 12c inserts into the opening of esophagus E and blocks or covers the opening of esophagus E. Grip portion 14h near proximal end 14a of upper blade 14 is spaced apart from handle 18 on proximal end 12a of lower blade 12. With the patient P lying horizontal with the neck extended, handle 18 and grip portion 14h are in an essentially vertical position. At the same time flat or horizontal portion 12d of lower blade 12 and flat or horizontal portion 14d of upper blade 14 are in a relatively horizontal position.

Figure 5:
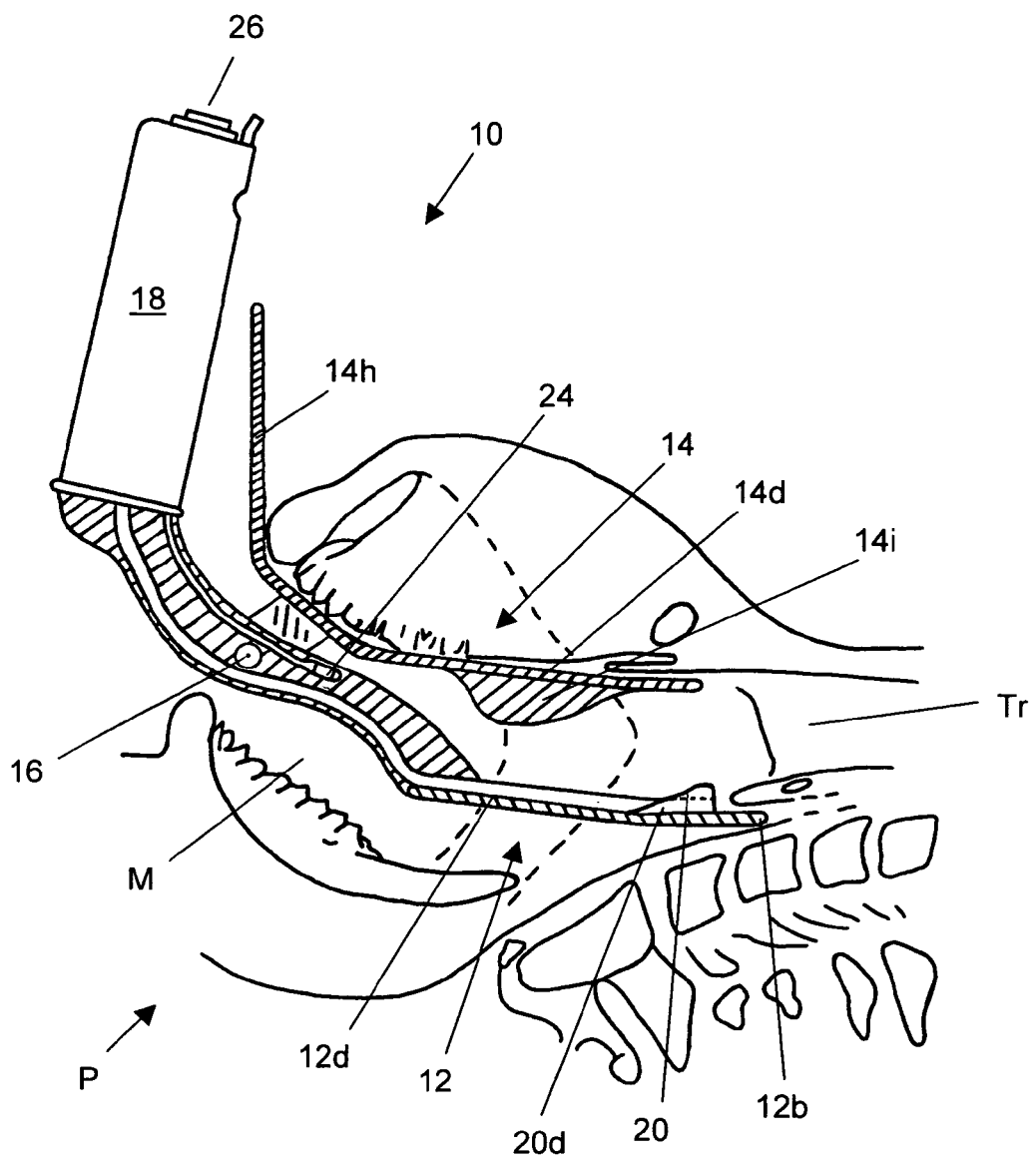
FIG. 5 is a side view of the laryngoscope of FIG. 1 inserted through a patient's mouth with the laryngoscope in the open position, according to the present invention.

Turning to FIG. 5, laryngoscope 10 is shown still inserted in mouth M of patient P, but in the open position. By squeezing handle 18 and grip portion 14h closer together, upper blade 14 pivots on pin 16 away from lower blade 12, which increases the distance between distal ends 14b and 12b on upper blade 14 and lower blade 12, respectively. Tongue guard 14i tends to hold the tongue to one side out of the way, and a relatively clear passageway is formed through which an intubation tube can be guided into the trachea Tr. The intubation tube, which is not shown, would slide on the upper surface of flat or horizontal portion 12d of lower blade 12, ride up on incline surface 20d of arytenoid bumper 20, pass through the larynx and into trachea Tr. Lamp 24 can be illuminated by pressing switch 26 with a thumb, provided a battery is in the circuit with lamp 24 and switch 26. The battery can be stored in a compartment within handle 18.

After successful insertion of the intubation tube into the trachea Tr, laryngoscope 10 can be removed without disturbing the intubation tube, since upper blade 14 is hingedly connected to only one side of lower blade 12. The side opposing the hinged side is open, allowing laryngoscope 10 to be removed from mouth M of patient P while the intubation tube remains in place. Prior art laryngoscopes with dual hinges had the intubation tube passing through a tunnel such that the prior art laryngoscope could not be removed laterally from the intubation tube.

2. Operation of Invention.

Before inserting laryngoscope 10 into the mouth of a patient, suction fitting 22c of laryngoscope 10 in FIG. 1 is connected to a vacuum source, such as is typically provided as either a wall unit or a portable unit. Switch 26 on handle 18 is depressed to turn lamp 24 on and illuminate the airway as the caregiver is intubating the patient.

As shown in FIG. 4, laryngoscope 10 is then inserted into mouth M of a patient P lying supine. Initially, the laryngoscope is in a closed position as illustrated in FIG. 4. The distal end 12b of lower blade 12 slides along the side of the tongue back toward the esophagus E. The esophageal obturator 12c on the distal end 12b of lower blade 12 enters or covers the esophagus E blocking or obstructing the esophagus E so that the patient does not pass vomit into the lungs. Where there is a concern that the patient is retching or vomiting, which may injure the esophagus if the esophagus is blocked or obstructed, the esophageal obturator can instead include a tube (not shown), in addition to or in place of suction conduit 22, of appropriate size for passing liquid and small particles outside of the patient's body.

Arytenoid bumper 20 shown in FIG. 1 serves as a stopper and tactile indicator to let the caregiver know when to stop inserting laryngoscope 10. This can help prevent damage to soft tissue. The presence of arytenoid bumper 20 is the preferred embodiment for the present invention. Arytenoid bumper 20 bumps into and rests against the arytenoid cartilage, and arytenoid bumper 20 and esophageal obturator 12c are adapted so that esophageal obturator 12c obstructs the esophagus while arytenoid bumper 20 rests against the arytenoid cartilage. The flat or horizontal portion 12d of lower blade 12, flat or horizontal portion 14d of upper blade 14, esophageal obturator 12c, and arytenoid bumper 20 are preferably coated with plastic or a soft rubber to reduce the risk of injury to soft tissue. The flat or horizontal portion 12d and particularly flat or horizontal portion 14d may be made of a semi-rigid material, which is strong enough to move soft tissue out of the way to provide an opening for passage of an endotracheal tube (not shown), but sufficiently soft and pliable to conform to the tissue and reduce risk of injury to tissue.

Once the laryngoscope 10 is properly seated above or slightly inside the esophagus, grip portion 14h as shown in FIGS. 4 and 5 can be squeezed toward handle 18 to create an opening between distal ends 12b and 14b of blades 12 and 14. To further reduce the risk of injury to soft tissue, grip portion 14h and handle 18 are preferably adapted to touch when the upper and lower blades are opened to provide a stopping point to prevent over opening the blades and injuring soft tissue.

As can be best seen in FIG. 2, upper blade 14 is separated from lower blade 12 because hinge portion 14f of upper blade 14 has an L-shaped tab 14j to which pin 16 is connected. Hinge portion 14f is adapted to provide spacing between upper blade 14 and lower blade 12 and is placed closer to the proximal end than the distal end so that flat or horizontal portion 12d and 14d of lower and upper blades 12 and 14, respectively, open in a more nearly parallel fashion rather than in a scissor-like fashion. The hinge is preferably used to provide a pivotal action that maintains flat or horizontal portions 12d and 14d in more nearly parallel orientation as the blades are separated. This can also be accomplished by using a hinge of the type adapted for this purpose rather than a single pin shown in the figures. The hinge is typically on the left side as the laryngoscope is typically held in the left hand while the right hand is used to insert an endotracheal tube, but this could be reversed for a right-handed laryngoscope.

In the event that suction is necessary to remove secretions or emesis, suction break 22d in handle 18 provides a finger control for regulating the amount of vacuum provided. A caregiver's finger can be placed over suction break 22d to increase the vacuum (lower the absolute pressure) or removed so that there is no vacuum or suction at suction ports 22a and 22b. One, two or more openings can be used as suction ports, and two or more openings are preferred so that in the event that one opening becomes blocked, another opening is available.

Suction conduit 22 begins at suction fitting 22c passes through handle 18 and across lower blade 12 and enters arytenoid bumper 20 at point 22f. In the preferred embodiment, suction conduit 22 will split into two channels which exit arytenoid bumper 20 at suction ports 22a and 22b. In another embodiment, the arytenoid bumper can serve as a manifold in the location of distal end 12b, where the arytenoid bumper is hollow with one or more openings to serve the purpose of suction ports 22a and 22b with suction conduit 22 connected to arytenoid bumper 20 for applying vacuum to a hollow chamber inside arytenoid bumper 20.

Laryngoscope 10 provides rapid and accurate intubation because suction can be applied at the same time that an endotracheal tube is inserted into a patient's airway. In the past, this was typically a two-step process with a first step of suctioning to remove mucus, vomit, blood and the like and a second step of intubation. Where precious seconds may count in saving the life of a patient, laryngoscope 10 provides a more rapid and more effective method of intubation and suction in a single step. The present invention allows operation of suction with the same hand holding the laryngoscope. This is a significant improvement over the prior art because it allows caregivers to immediately use the hand not holding the laryngoscope for intubation without wasting time manipulating a suction device with that hand prior to handling the intubation tube. Those familiar with the current art will immediately understand this advantage.

Once the airway is cleared of secretions or emesis (if necessary), an endotracheal tube would be passed down beside vertical portion 12e and over flat or horizontal portion 12d of lower blade 12 and deflected up the inclined surface 20d of arytenoid bumper 20 into the trachea. Although a stylet could be used to pass the endotracheal tube, it will likely be unnecessary since the ramp created by inclined surface 20d directs the tube into the trachea.

Once the endotracheal tube is in place, the laryngoscope 10 can easily be removed from the mouth M with one smooth motion without disturbing the endotracheal tube. With other laryngoscopes a caregiver must remove the adapter fitting found on the proximal end of an endotracheal tube that connects the tube to an oxygen source in order to slide the laryngoscope up off the endotracheal tube. This can waste precious time when a patient is in dire need of oxygen. Another advantage of the present invention is the endotracheal tube can be attached to an oxygen source and oxygen can be flowing through the tube during the intubation process. Once the tube is in place, a patient will immediately be receiving oxygen.

After use, laryngoscope 10 will need to be cleaned. Switch 26 and handle 18 are preferably sealed, so that laryngoscope 10 can be immersed in a disinfectant solution. Alternatively, handle 18 can be removable or can be cleaned otherwise, as absolute sterilization is not required since a patient's mouth is not sterile.

3. Description and Operation of Alternative Embodiments.

Various modifications can be made to the laryngoscope of the present invention. While it is preferably made of surgical stainless steel, it can be made of plastic or other materials and can be disposable rather than reusable. A lamp can be placed in the handle with a fiber optic cable extending toward the distal end, and the fiber optic cable can be disposable. The blades can be made of a clear plastic so as to serve as a light tube as taught by Minson in U.S. Pat. No. 5,938,591. Another alternative is to have a reusable handle that attaches to removable and disposable blades. The blades would attach to handle 18 at exit point 22e shown on FIG. 1. This would allow for a less expensive and more compact laryngoscope system consisting of various sizes of disposable blades. It would also allow caregivers to quickly intubate multiple patients during a multiple victim emergency.

Arytenoid bumper 20 is a preferred, but optional, feature as is esophageal obturator 12c and suction conduit 22. Tongue guard 14i is another optional feature. The components of the laryngoscope can be made in different ways. For example, with reference to FIG. 1, an edge of lower blade 12 could be rolled to form a tube, which can be sealed to provide a suction line along the length of lower blade 12. Cost and efficiency of manufacture should be taken into account, and a separate tube as shown in FIG. 1 fixed or adhered to lower blade 12 may be a more practical solution.

Laryngoscope 10 is preferably used as a suction device by applying a vacuum tube to suction fitting 22c and suctioning fluid and solids through suction ports 22a and 22b, preferably with a finger, possibly covering, partially covering or leaving open the suction break 22d for controlling the vacuum at suction ports 22a and 22b. Although the preferred embodiment is to have two openings in arytenoid bumper 20, the openings may also exit lower blade 12 at esophageal obturator 12c. Another embodiment is to have either one opening or multiple openings located on the distal end 12b of lower blade 12. In addition, suction conduit 22 may be made of a single or jointed tube.

Various commercial embodiments of the present invention can be made, including, for example, a base model with a single inventive aspect, a deluxe model with all inventive aspects, and intermediate models with combinations of some but not all inventive aspects. The material of construction can be varied, which will vary the cost. Features such as the handle enclosing a battery can be eliminated or modified. The present invention also provides various methods for intubating a patient, including suctioning with a laryngoscope while intubating.

Thus the reader will see that the present invention provides an inexpensive laryngoscope that will make intubation a quicker and easier process for caregivers. This laryngoscope ensures proper placement of an endotracheal tube by blocking the esophagus and by providing a deflecting ramp to properly deflect the endotracheal tube into the trachea during insertion. Damage to tissues is minimized by the arytenoid bumper that provides resistance, felt by the user, when the laryngoscope has been inserted to the proper depth, as well as by the limitation on the distance the dual blades of the laryngoscope may be opened in a patient's mouth inherent in the arrangement of the handle and the hand grip used to open the blades. The laryngoscope also provides for easy removal after tube placement due to its single-sided hinge design. Other advantages include a tongue guard to move the tongue out of the field of vision, and the ability to suction the patient more easily and effectively by integrating the suction apparatus into the laryngoscope.

In conclusion, it is understood the dual bladed laryngoscope with esophageal obturator described herein and shown in the drawings represents only a presently preferred embodiment of the invention. Indeed, various modification and additions may be made to such embodiment without departing from the spirit and scope of the invention. It is realized that changes are possible within the scope of this invention and it is further intended that each element or step recited in any claims is to be understood as referring to all equivalent elements or steps. The claims are intended to cover the invention as broadly as legally possible in whatever form it may be utilized. The scope of the invention should be determined by the following claims.

What is claimed is:

1. A laryngoscope, comprising:
   a lower blade;
   an upper blade that pivots away from the lower blade, wherein the lower blade has a distal end adapted as an esophageal obturator; and
   an arytenoid bumper having a wedge shape on the lower blade proximate to the esophageal obturator which together with the esophageal obturator obstructs the opening to the esophagus.

2. The laryngoscope of claim 1, wherein the lower and upper blades have opposing sides, and wherein the proximal end of the blades and at least one lateral side of the blades are open allowing the laryngoscope to be removed laterally over a tube inserted into the airway.

3. The laryngoscope of claim 1, further comprising illumination of the distal end of the laryngoscope.

4. The laryngoscope of claim 2, further comprising an arytenoid bumper providing a ramp to guide an intubation tube in the general direction of the vocal cords and obstructing the opening to the esophagus, and the esophageal obturator enters into and blocks the esophagus.

5. The laryngoscope of claim 4, wherein the arytenoid bumper and/or the lower blade where the arytenoid bumper is attached to the lower blade is wider than a portion of the lower blade adjacent to the arytenoid bumper.

6. The laryngoscope of claim 1, further comprising a handle and a hand or finger grip on the proximal end of one or more blades wherein the hand grip portion can be moved closer to or farther away with respect to the handle to open or close the distal ends of the lower and upper blades with respect to one another.

7. The laryngoscope of claim 1, wherein the lower and upper blades are removable.

8. The laryngoscope of claim 1, wherein the lower and upper blades are disposable.

9. The laryngoscope of claim 1, further comprising a tongue guard fixed to the upper blade adapted to form a 3-sided passageway defined by the tongue guard, the upper blade and the lower blade.

10. The laryngoscope of claim 1, further comprising a suction tube integrated into the lower blade with one or more fixed suction ports at the distal end of the lower blade for providing a conduit for suctioning during intubation.

11. The laryngoscope of claim 1, further comprising illuminating a distal end of the laryngoscope.

12. A laryngoscope, comprising:
a lower blade; and
an upper blade that pivots away from the lower blade, wherein the proximal end of the blades and at least one lateral side of the blades are open allowing the laryngoscope to be removed laterally over a tube inserted into the airway.

13. The laryngoscope of claim 12, further comprising an esophageal obturator on a distal end of the lower blade.

14. The laryngoscope of claim 12 further comprising an arytenoid bumper fixed to the lower blade wherein the arytenoid bumper has a wedge shape for providing a ramp to guide an intubation tube in the general direction of the vocal cords and to block the esophagus.

15. The laryngoscope of claim 12, further comprising a handle and a hand or finger grip on the proximal end of one or more blades, wherein the handle and the hand grip are adjacent to one another, and wherein the distance between the handle and the hand grip can be reduced to spread apart the distal end of the lower and upper blades with respect to one another.

16. The laryngoscope of claim 12, further comprising a tongue guard fixed to the upper blade adapted to form a 3-sided passageway defined by the tongue guard, the upper blade and the lower blade.

17. The laryngoscope of claim 12, further comprising a tube integrated into the lower blade with one or more fixed suction ports at the distal end of the lower blade for suctioning mucus, saliva, or emesis during intubation.

18. A laryngoscope, comprising:
An upper and lower blade; and
a tube integrated into the lower blade with one or more fixed suction ports integrated into a wedge at the distal end of the lower blade, wherein the tube and suction ports are adapted for applying suction and the blade is adapted for use in intubating a patient.

19. The laryngoscope of claim 18, wherein the suction tube is adapted for receiving a vacuum source on a proximal end, the suction tube having a distal end with one or more openings and being adapted for suctioning while inserting an intubation tube into the patient's air way.

20. The laryngoscope of claim 18, wherein the upper blade pivots away from the lower blade.

21. The laryngoscope of claim 20, wherein the proximal end of the blades and at least one lateral side of the blades are open so that an intubation tube may be removed laterally from the lower and upper blades.

22. The laryngoscope of claim 20, further comprising an esophageal obturator on a distal end of the lower blade adapted for obstructing a patient's esophagus.

23. The laryngoscope of claim 20, further comprising an arytenoid bumper secured to the lower blade near the distal end of the lower blade and having a ramp or wedge shape adapted to direct an intubation tube through the patient's larynx into the patient's trachea.

24. The laryngoscope of claim 20, further comprising a tongue guard fixed to the upper blade adapted to form a 3-sided passageway defined by the tongue guard, the upper blade and the lower blade.

25. A method for intubating a patient, comprising the steps of: inserting a dual-bladed laryngoscope into or through the patient's mouth until an arytenoid bumper stops against the arytenoids; obstructing the esophagus with an arytenoid bumper; squeezing a grip to pivot the upper blade away from the lower blade; and inserting an intubation tube through the laryngoscope.

26. The method of claim 25, wherein the laryngoscope has an upper blade and a lower blade, and wherein the lower blade is adapted to have an esophageal obturator on its distal end to assist in obstructing the esophagus.

27. The method of claim 25, further comprising locating the proper position of the laryngoscope by resting an arytenoid bumper against the arytenoid cartilage of the patient.

28. The method of claim 27, wherein the laryngoscope has an upper blade and a lower blade, and wherein an arytenoid bumper having a ramp shape is fixed to the inside surface of the lower blade and is adapted to direct the intubation tube off of the inside surface of the lower blade and into the patient's larynx, further comprising deflecting an intubation tube off the inside surface of the lower blade into the patient's larynx toward the vocal cords.

29. The method of claim 25, wherein the laryngoscope has an upper blade and a lower blade, further comprising holding the patient's tongue outside of a channel formed between the blades of the laryngoscope with a tongue guard.

30. The method of claim 25, further comprising illuminating a distal end of the laryngoscope.

31. The method of claim 25, further comprising removing the laryngoscope from the patient's mouth laterally over the tube inserted in the airway due to the proximal end of the blades and at least one lateral side of the blades being open.

32. The method of claim 25, wherein the laryngoscope has a handle and a hand or finger grip on the proximal end of one or more blades, and wherein the hand or finger grip and handle are providing a stop that prevents the two blades from opening more than a predetermined distance.

* * * * *